(12) United States Patent
Feine

(10) Patent No.: US 6,503,081 B1
(45) Date of Patent: Jan. 7, 2003

(54) ULTRASONIC CONTROL APPARATUS AND METHOD

(76) Inventor: James Feine, P.O. Box 2009, Bellaire, TX (US) 77402-2009

( * ) Notice: Subject to any disclaimer, the term of this patent is extended or adjusted under 35 U.S.C. 154(b) by 9 days.

(21) Appl. No.: 09/606,464

(22) Filed: Jun. 29, 2000

Related U.S. Application Data

(60) Provisional application No. 60/142,009, filed on Jul. 1, 1999.

(51) Int. Cl.$^7$ .............................. A61C 3/03; H01L 41/06
(52) U.S. Cl. ................................... 433/119; 310/316.01
(58) Field of Search ............................... 433/118, 119; 310/316.01

(56) References Cited

U.S. PATENT DOCUMENTS

| | | | |
|---|---|---|---|
| 4,063,557 A | 12/1977 | Wuchinich | 128/276 |
| 4,371,816 A | 2/1983 | Wieser | 318/116 |
| 4,375,961 A * | 3/1983 | Brooks | 433/4 |
| 4,425,115 A | 1/1984 | Wuchinich | 604/22 |
| 4,703,213 A | 10/1987 | Gäsler | 310/316 |
| 4,820,152 A | 4/1989 | Warrin et al. | 433/86 |
| 5,059,122 A | 10/1991 | Hetzel | 433/118 |
| 5,121,023 A | 6/1992 | Abel | 310/316 |
| 5,451,161 A | 9/1995 | Sharp | 433/119 |
| 5,654,605 A | 8/1997 | Kawashima | 310/316 |
| 5,730,594 A | 3/1998 | Sharp | 433/119 |
| 5,754,016 A | 5/1998 | Jovanovic et al. | 318/118 |
| 5,889,350 A | 3/1999 | Yamamoto | 310/316 |
| 5,895,997 A | 4/1999 | Puskas et al. | 310/316 |
| 5,897,569 A | 4/1999 | Kellogg et al. | 606/169 |
| 5,927,977 A | 7/1999 | Sale et al. | 433/86 |
| 6,002,195 A | 12/1999 | Puskas | 310/325 |
| 6,078,124 A | 6/2000 | Furuhashi et al. | 310/318 |

FOREIGN PATENT DOCUMENTS

| | | |
|---|---|---|
| EP | 0270819 | 10/1987 |
| EP | 0424685 | 9/1990 |
| WO | 9811844 | 3/1998 |

* cited by examiner

*Primary Examiner*—John J. Wilson
(74) *Attorney, Agent, or Firm*—Daniel N. Lundeen; Lundeen & Dickinson, LLP

(57) ABSTRACT

The present invention relates to a microprocessor-controlled ultrasonic control apparatus used to sweep a range of operating frequencies and to identify, store and tune to the resonant frequency of a magnetostrictively driven handpiece. This allows the user to change tip systems as desired and the device is not limited to a preset or switch selectable frequency. The unit automatically finds and adjusts to the frequency which corresponds to the resonant acoustic frequency of the magnetostrictive coil insert tip system.

12 Claims, 2 Drawing Sheets

ULTRASONIC CONTROL APPARATUS AND METHOD

RELATED CASES

This application claims the benefit of U.S. Provisional Application No. 60/142009, filed Jul. 1, 1999.

BACKGROUND OF THE INVENTION

The present invention relates to an ultrasonic control device and, more specifically, to a microprocessor controlled ultrasonic generator for use with a magnetostrictive element, which automatically adjusts to the resonant mechanical frequency of a tip-insert combination of a dental scaler or the like, thereby allowing the user to substitute or replace tips as desired. Upon startup or reset, the controller automatically steps through a range of frequencies, storing the resonant frequency for the tip system. The controller thereafter maintains the tip system in use at or near the resonant frequency of the tip providing the most efficient use of the device.

1. Prior Art

Warrin, in U.S. Pat. No. 4,820,152, teaches the use of a multi-purpose handpiece which is capable of sensing the type of tip insert being utilized and adjust or tune the circuitry accordingly.

Hetzel, in U.S. Pat. No. 5,059,122, teaches the use of tuning the frequency of an oscillator to match the feedback from the response of the mechanical resonant frequency of the dental insert.

Sharp, in U.S. Pat. No. 5,730,594, teaches an ultrasonic dental scaler which is driven by a switch selectable circuit to either automatically tune to the resonant frequency or to permit manual adjustment of the frequency of the oscillator. Sharp, in U.S. Pat. No. 5,451,161 teaches automatically tuning an oscillating circuit to match the resonant frequency of the tip insert.

2. Background

Ultrasonic medical devices, such as dental scalers, driven by coils surrounding magnetostrictive elements, are well known in the art. In such ultrasonic devices, vibrational motion results from an oscillating current being supplied to the coil which induces a magnetostrictive element to begin oscillating. The oscillation of the magnetostrictive element translates into flexural or elliptical motion of an insert tip. The magnetostrictive element is affixed at a node to an element, generally described as a velocity transducer, which translates the vibration to the distal tip of the insert system. In dental hygiene applications, the tip contacts accumulated calculus on the tooth surface to dislodge the calculus. The tip also provides a pathway for irrigating the area where the tip is used by dispensing a liquid, most often water, through or over the surface of the tip. The flow of liquid through the hand piece also dissipates heat generated by Joule heating of the coil/magnetostrictive element.

Ultrasonic scalpels may also be driven by the vibration caused by an energized coil around a stack of magnetostrictive plates, such as nickel or nickel alloy, which transmits its vibratory motion through an intermediate element, called a velocity transducer, to a cutting tip. Some prior art devices controlled current levels to the energizing coil of the magnetostrictive element by placing secondary pickup coils to measure power transfer. The present invention does not require any secondary coils to control the vibration of the tip. Some prior art devices devised numerous methods of determine the type of tip system in use. The present invention automatically adapts to the natural acoustic frequency of the tip system being used permitting a wide variety of frequency response to a variety of tip systems.

Other prior art devices allowed only a switch-selectable frequency choice. In the present invention, the frequency tunes automatically from the feedback received from the magnetostrictive tip system in operation.

Some other prior art dental scaler devices automatically sought a higher resonant frequency within the designed bandwidth around one or two design frequencies. The automatic tuning feature of these prior art devices provided unstable tip operation because these circuits were constantly changing frequency during the procedure, providing an uncomfortable experience for the patient. In the present invention, the resonant frequency is locked into the control circuit to provide smooth operation.

SUMMARY OF THE INVENTION

The present invention provides a microprocessor to automatically sense the appropriate mechanical resonant frequency by its effect on the power consumption of the power supply, lock on to that frequency, optionally allowing the user to offset from the resonant frequency and variably adjust the amplitude of the tip system with minimal user intervention. Heretofore, so far as known to applicant, the design of the magnetostrictive devices was limited to the frequency of the driving circuitry. The physical characteristics of the magnetostrictive stack, velocity transducer and tip defined the resonant frequency of the system that was required to be matched to the oscillating frequency of the coil. The present invention reduces, if not eliminates, this problem. In operation, the technician would insert the tip into the hand piece, reset the microprocessor (alternatively, for example, from the front panel, the foot switch, a handpiece switch, a voice command, or upon the passage of a preset time interval measured by the microprocessor), the microprocessor would then sweep or step through a range of frequencies preset in the memory of the microprocessor and selectively tune the system to its maximum or resonant acoustic frequency. The front panel of the system would provide means for selectively setting an offside frequency (from the resonant frequency) thereby increasing the comfort of the patient or reducing the vibration of the tip. The appropriate resonant acoustic frequency would be determined upon boot or reset of the microprocessor and would not thereafter be changed unless the operator desired to change the setting or a new tip system was installed in the hand piece. This feature would allow technicians to choose the appropriate tip system to achieve the maximum efficiency and comfort in the dental scaling, polishing or surgical process.

The present invention allows the user to control, for example, a dental scaler tip system, an ultrasonic polisher, a surgical scalpel, or a feline urinary tract probe (each having a significantly different resonant acoustic frequency profiles) on the handpiece and the controller will adjust automatically to the most efficient resonant frequency. This invention allows a large variation of driven elements (for example, tips, polishing stones, surgical blades, etc.), greatly increasing the functionality of ultrasonic usage. Other uses of the ultrasonic controller capable of automatically adapting to a broad spectrum of resonant frequencies may be suggested.

For example, in the feline urinary tract probe, a long thin hollow probe was attached to the end of a low frequency (and low power) magnetostrictive stack to break up and flush away urine crystals in male cat's urinary tracts. The probe is not easily controlled on a standard ultrasonic generator at 25 or 30 kHz. The present system would automatically compensate for the natural acoustical resonance of the tip system and determine the appropriate setting, while providing a very smooth and controllable ultrasonic activity, despite the possibility of different probe lengths and shapes.

DETAILED DESCRIPTION OF THE INVENTION

Figure 1:
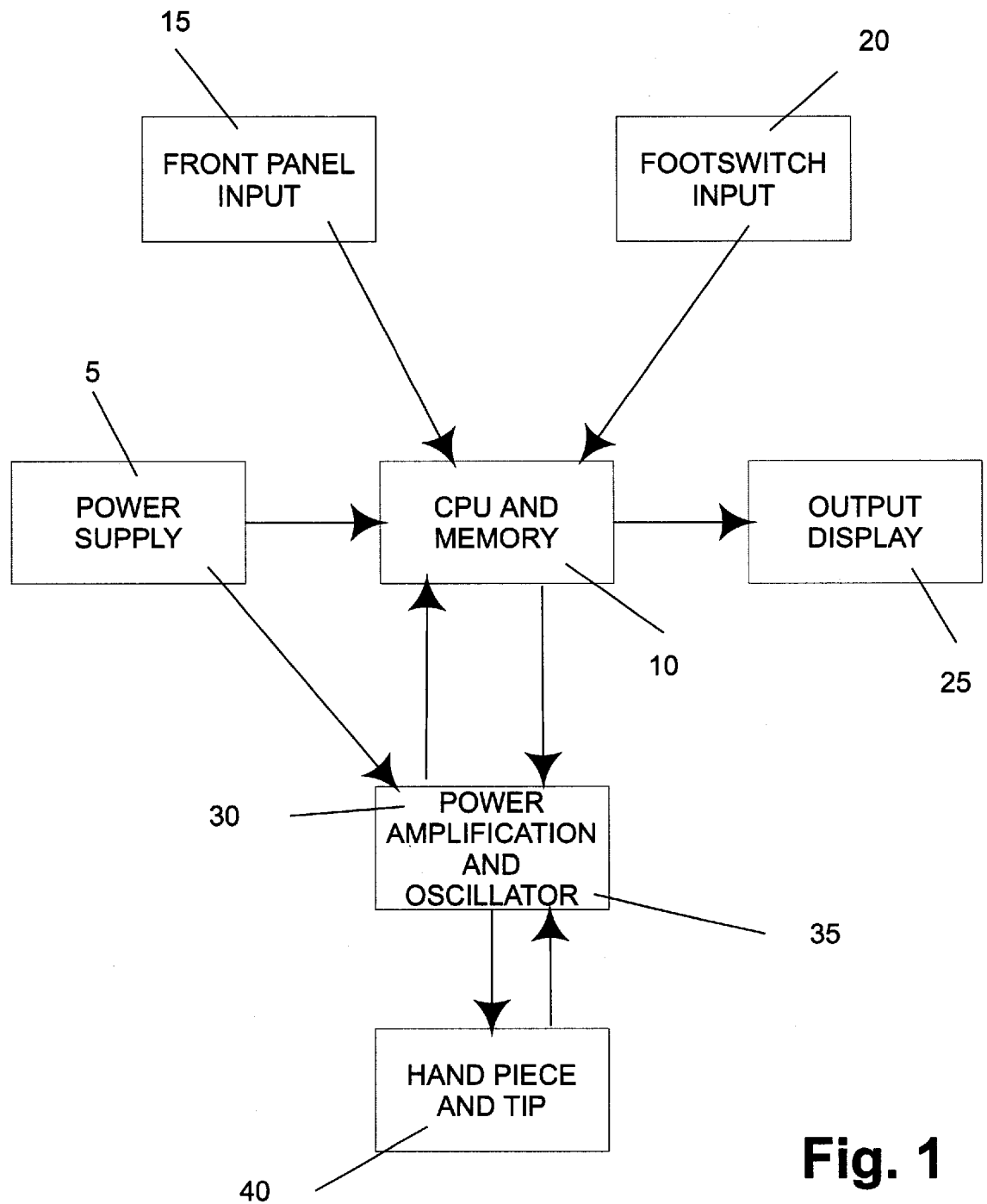
FIG. 1 is a schematic drawing according to one embodiment of an ultrasonic device control system of the present invention.
Figure 1:
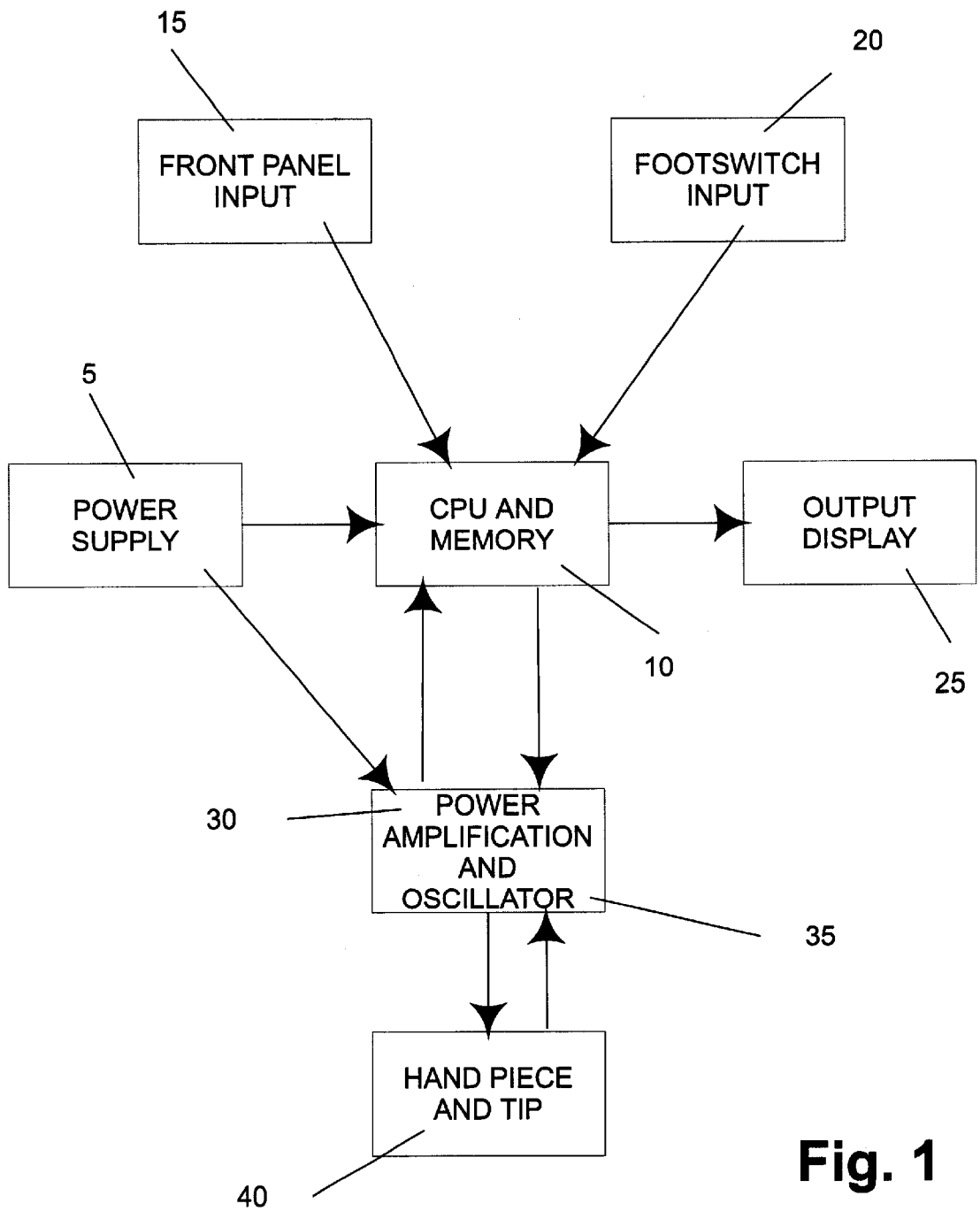

With reference to FIG. 1, the microprocessor 10 is preferably a solid state programmable device; namely, an 8051 chip manufactured by Intel Corporation of Santa Clara, Calif. This microprocessor chip is particularly suited for relatively low power operation, and for combining the several desirable features of the ultrasonic scaler control apparatus of the present invention. This chip may be readily interfaced with complementary peripheral chips to provide the frequency sweep and power control functions described herein. However, it is understood that other microprocessors or a custom made chip can be utilized in accordance with the broad aspects of the present invention. It is only necessary that the computing capacity and power requirements be suitable for carrying out the functions as described with respect to the control circuitry and functions described herein.

The power supply to the system is provided by power supply 5 that, in a preferred embodiment, includes a transformer that has as its input the standard AC power supplied in most offices and clinics. The transformer reduces the line voltage to approximately 15 to 25 volts AC under load and also provides minimal circuit isolation to the balance of the circuitry. The transformer output can be coupled to a bridge rectifier to convert the AC to DC power. Capacitors can be used, in a manner well known to those having ordinary skill in this art, to smooth the low voltage and can provide a fuse to provide further protection of the circuit from transient voltages. This power can also be supplied to a variable voltage regulator. The power to the unit can be controlled, for example by either a power level control footswitch or an on/off footswitch and/or a panel-mounted power controller. Other means for controlling power can also be used.

The power supply provides both the power to drive the coil contained in the hand piece to vibrate the magnetostrictive element that provides the tip with its energy, and the microprocessor and peripheral control chips in a manner well known in the art.

The microprocessor 10 is controlled by input devices connected to the front panel 15 which consist of switches for initial startup, reset, and can provide an optional keypad for the input of data by the user. The microprocessor 10 can also be controlled by footswitch 20 that provides a microswitch for power on and reset functions and to optionally increment or decrement power settings as need by the operator. A display unit 25 may also be provided for the system consisting of either light emitting diodes (LEDs) to indicate the current status of the tip system or a liquid crystal diode (LCDs) display describing the state of the system and the current optimum frequency and power settings, as well as providing operating instructions to the operator for diagnostic and inputting of settings into the programmable microprocessor 10. Further, the microprocessor may provide a timer circuit to shut the power system down and indicate the error condition on the control panel or by audible signal if the footswitch remains depressed longer than a preset period. For example, if there is no change in movement of the power control footswitch for ten minutes, or if the on/off footswitch remains depressed too long, for example fifteen minutes, the error condition is activated. The circuitry may also provide an override switch, such as a push button, with an integral lamp, on the control console, or spring loaded switch to reset the system automatically rather than going through a complete restart of the system.

The sweep oscillator circuit 35 function is carried out by peripheral chips complementary to the 8051, but may also be fabricated from discrete components and readily interfaced with the processor. The sweep is initiated either at start up, reset or periodically when the tip system is not in use to recalibrate and retune the system. The sweep oscillator steps through the frequencies starting with the low (or high) frequency found in the programmable read only memory (PROMs) in the system as described herein; or, alternatively, at a frequency user-set from the front panel at the user's discretion. The frequency steps can be either preprogrammed or user set depending on the preferences of the operator and each unit will default to the factory setting of 50 Hz per step. Other frequency steps sizes can be used and stored in the PROMs.

The power amplifier 30, which as previously noted may be either a complementary peripheral chip or integrated circuit or a separate discrete component circuit, is used to lock onto a resonant frequency once this frequency is isolated and hold the tip system at that power consumption level irrespective of the load being placed on the tip. This permits, as noted herein, the lowest and therefore most comfortable level of power to be used for each tip system. Additional power can be delivered to the tip by user control or by the automatic adjustment from the power amplifier circuitry.

The hand piece and tip system 40 (not shown in detail) is an integrated unit consisting of a hollow hand piece which accomodates a coil into which is fitted a magnetostrictive insert typically consisting of a number of nickel or nickel alloy leaves. The nickel or nickel alloy plates are affixed to a velocity transducer which is held at the distal end of the hand piece. Extending from the transducer is a tip which provides the fluid passage. Fluid, typically water (but other medicaments or air could also be used), is conducted around the leaves within the coil serving to carry off heat generated by the activated coil and to flush the calculus from the tooth surface. In an ultrasonic scalpel application, water may be circulated through the handle of the handpiece and returned to the source to cool the magnetostrictive coil or used to irrigate the wound as required or desired by the application.

The control apparatus is activated upon power up by switch from the front panel of the ultrasonic generator. Upon power on or reset, also initiated on the front panel or on the foot switch, the sweep generator is activated which determines the preset low and high frequency, which can be preset by the factory (or by input from the front panel as desired). In a preferred embodiment, these are preset by factory settings at 5 kHz and 90 kHz, which range covers the resonant frequencies of all known magnetostrictive ultrasonic system inserts on the market. During the initial startup, the power consumption of the tip system is measured and the frequency incremented to the coil driving the tip system by a fixed amount. The power consumption of the coil is again measured and compared against the prior step's measured power. This new value is stored in memory and the process of incrementing the frequency and measuring the power consumption and comparing to the prior power consumption reading is repeated. Once the power consumption declines with an increase in frequency, a resonant frequency is identified and this frequency value is stored again in memory as an optimal value. If the sweep has not completed its run from preset low frequency to preset high frequency, the increment measure process is repeated until completed and the highest power consumption corresponding to the maximum frequency is stored.

The power consumption of the coil can be measured and controlled in a variety of ways well known to those in the art. For example, the microprocessor can be programmed to sense, by means of compatible peripheral chips or appropriate circuitry, signals corresponding to the inductance, reluctance and capacitance and/or the power derived from these elements for the particular combination of tip insert and coil system. The phase angle between the current and voltage of the coil/handpiece system can be measured and adjusted to bring the coil into resonance. Slope detection circuits can also be used to determine the maximum power transfer point since at the resonant frequency the slope of the frequency response curve is zero. Any of the foregoing methods can be used to determine the resonant frequency.

An additional feature of the preferred embodiment allows the operator/technician to set an offside frequency setting for the comfort of the patient or convenience of the operator. The acoustic resonant frequency has an operating effective bandwidth of ±1500 Hz from the maximum. This permits the operator to reduce the power to the coil sufficient to decrement the tip vibration slightly from its maximum deflection. In the dental scaler application, if calculus on the tooth surface appears resistant to the frequency/power setting, the foot switch can be further depressed to increase the amplitude of the tip, allowing more power to break up the deposit and thereafter permit reduction to the prior off-peak comfort level.

The automatic power level control module locks on to and retains the tip system at the pre-set power while the tip is in use to maintain vibration in the tip. Extremely low power settings can thus be used despite pressure on the tip while in contact with the tooth surface which would otherwise stall the vibration.

The system would also provide themocouple connections in both the handpiece and the power amplification circuitry to detect excessive heat buildup. If the sensed temperature exceeded a preset temperature (which may be operator selectable), the power system would be shut down and a warning light or sound would warn the operator of the condition. Excessive heat may result from inadequate fluid flow through the handpiece caused by kinking of the supply source or clogging of tubing. The system would provide an operator override such as a switch with integral lamp or other means to reset the system.

The present invention also permits the technician to install any tip system as may be desired by the technician. Since the resonant frequency of any given tip is a function of its composition, length and physical makeup, the sweep system readily and easily determines the appropriate resonant frequency for a tip within a second or two of reset.

Figure 2:
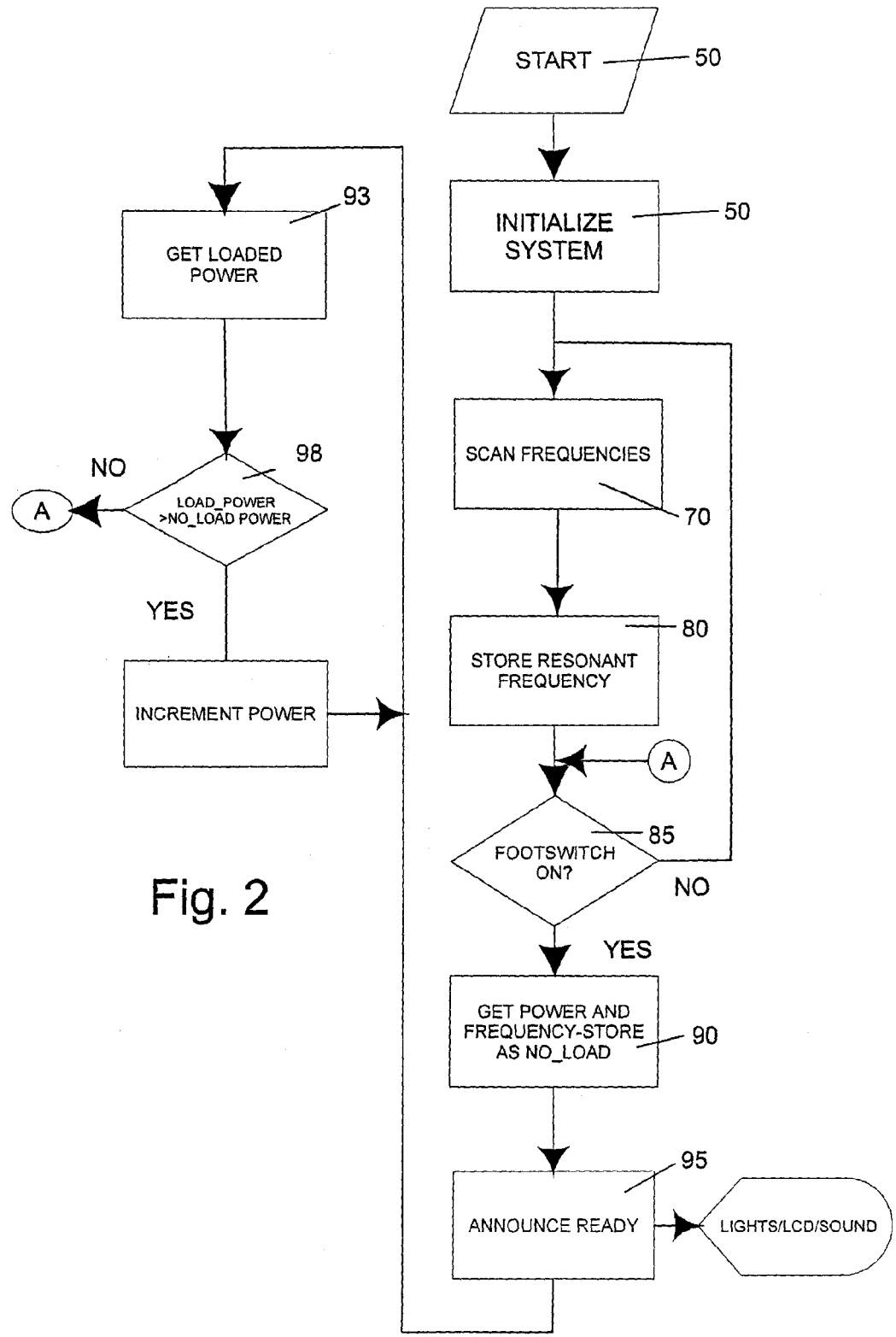
FIG. 2 is a logic or flow diagram according to one embodiment of an ultrasonic device control system of the present invention.

FIG. 2 is a logic diagram of the control software for the microprocessor controlled magnetostrictive device. The start 50 results from the user switching the power switch on the front panel. The power supply drives both the microprocessor and the power supplied to the coil that drives the magnetostrictive device. The system program goes through its startup diagnostics 60 and senses the presence of the tip system and the power consumed by it. These values are stored in the memory of the machine and the frequency scan sequence 70 is begun. This scanning takes place in micro seconds under normal circumstances and the operator will be generally unlikely to notice any delay in the ability to begin use of the device. Once the magnetostrictive stack begins to acoustically resonate, the power consumption will significantly increase. At some frequency, the power consumption begins to decline as higher frequencies are scanned. The last, highest frequency 80 and the power consumption at that level are stored as control variables.

The system next attempts to detect whether the user has depressed the footswitch 85. If the footswitch has been depressed, the system again senses the frequency and power supplied to the tip 90 as a no-load power and the system announces ready 95; for example, by lighting LED lamps on the console 96, or indicating ready on a LCD display, or by issuing a sound. The level of depression of the footswitch is constantly monitored in step 93 by the system. Power is increased in step 99 either if the power drops from the dampening effect of the user placing the tip system in use against a tooth in step 98 or by the operator depressing the power level control footswitch. This permits the operator to selectively increase the power beyond the initial power derived by the system at startup from the no-load tip system. The system will automatically retain the tip at the power setting derived from the optimum or resonant frequency at startup, but can be selectively increased as desired by the depression of the footswitch.

While the system can be set up to be operable without a foot switch to increase power to the tip (as for example, to clean excess calculus from teeth), most systems will be delivered with such a device. This is primarily to permit the operator to use the tip system at the lowest possible power setting to minimize pain to the patient or damage to the instruments without having to reach back to the front panel to increase power to the tip. Alternatively, an additional power control could be placed on the front panel to allow the user to selectively increase the power from the front panel, if an on/off footswitch is used instead of a power level control footswitch. Various combinations of these methods of control are well known to those skilled in the manufacture and design of such devices.

A pseudocode outline of a portion of the control software which may be stored on the microprocessor in PROM, together with all other default values such as the low frequency and high-frequency, along with the step size frequency, follows. It is noted that the use of microprocessors allows the flexibility to add significant control features by new programming that may be distributed and installed in the field. High level control programming languages including, for example, assembler, PLM (the Intel control programming language derived from PL-1), and a control version of C, are all available for programming the 8051.

A portion of the pseudocode for the control of the device is described as follows:

Pseudocode Outline of Control Software do while power on
start:
fetch low-frequency (ie. 5 kHz);
fetch high-frequency (ie. 90 kHz);

```
store low-frequency
store high-frequency scanloop module:
    get power-consumption (of tip system insert)
    store power-consumption;
    increment low-frequency by fixed step size (default at 50
        Hz)
    get power (at new incremented frequency)
    if power>prior power consumption;
        store frequency value as low-frequency
    else if less
        store frequency as optimum-frequency
    if optimum-frequency<high-frequency then
        continue increment (by fixed step size)
    else if optimum frequency>high-frequency
        store resonant-frequency=optimum-frequency
        go to PLC (power level control) module
    else go to scanloop module offset frequency module:
    if offset-frequency enabled
        fetch offset-frequency value (e.g. 1 kHz from front
            panel)
    else if offset frequency not enabled
        fetch default value (e.g. from PROM)
    calculate optimum-frequency less offset-frequency;
    reduce power to tip until frequency=(offset) optimum
        frequency;

PLC module:
        fetch optimum frequency
        sense power at that frequency;
        maintain the power level at that frequency.

footswitch override:
        if footswitch depressed then
            get increase level from footswitch
            increase power (to tip) proportional to footswitch
                increase
        if footswitch not depressed
            go to PLC module.
```

Although illustrative embodiments of the present invention are described herein with reference to the accompanying Figures, it may be readily appreciated that the invention is not limited to those precise embodiments and that various other changes or modifications may be effected by one having ordinary skill in the art without departing from the scope or spirit of the invention.

The present invention opens up a whole spectrum of possibilities for ultrasonic devices. The ultrasonic tool designer or operator is no longer constrained to a specific resonant frequency or narrow range of frequencies at which the tool will operate. Instead, the ultrasonic tool, if it has a resonant frequency, will have its resonant frequency accurately sensed and locked onto by the controller. In dental scalers, for example, virtually any combination of magnetostrictive element, velocity transducer and tip can be used, provided they can be compatibly mechanically coupled. The dental scaler insert is no longer limited in its design since the controller of this invention will find and lock on the natural resonant frequency of the system.

What is claimed is:
1. An ultrasonic control device for a magnetostrictive tip insert system comprising:
    a microprocessor control unit including logic for selecting an optimum power transfer point offset from a resonant frequency of the magnetostrictive tip insert system;
    a sweep oscillator circuit connected to and communicating with said microprocessor control unit to step through a range of frequencies and permit the microprocessor unit to determine power consumption of the magnetostrictive tip insert at a plurality of discrete frequencies and select the optimum power transfer point and
    a power amplifier communicating with said microprocessor control unit to maintain a power level at the frequency of the optimum power transfer point by adjustment of the power delivered to the magnetostrictive tip insert.
2. The ultrasonic control device of claim 1 further comprising:
    a front panel connected to and communicating with the microprocessor control unit for input of data for offside tuning of the frequency of the magnetostrictive tip insert.
3. The ultrasonic control device of claim 1 further comprising:
    a footswitch for selectively increasing the power to the magnetostrictive tip insert.
4. The ultrasonic control device of claim 1 further comprising:
    a display panel connected to and communicating with the microprocessor control unit for receipt of visual output from the control system.
5. An ultrasonic computerized control apparatus comprising:
    input means:
    power means responsive to said input means;
    computer means activated by said power means to receive input signals including software for offset tuning to fix an operating frequency offset from a resonant frequency; and process said signals including software for offset tuning to fix an operating frequency offset from a resonant frequency;
    memory means for supplying a preselected range of values and for storing values equivalent to a variety of frequency values;
    operating means responsive to said computer means to step through a range of frequencies;
    power amplifier means responsive to said computer means for changing the power to an ultrasonic dental scaler including a magnetostrictive tip insert while maintaining the offset operating frequency; and
    means for connecting the power amplifier to the ultrasonic dental scaler.
6. An ultrasonic dental scaler apparatus comprising:
    conductors to an ultrasonic dental scaler including a magnetostrictive tip insert;
    a power amplifier coupled to said conductors for delivery of variable power at variable frequency;
    a sweep oscillator coupled to said power amplifier for stepping the frequency from a preset low to a preset high to determine a primary resonant frequency of the ultrasonic dental scaler;
    detection logic and memory to lock on to the resonant frequency detected and to store the value of the resonant frequency;

offside tuning logic for delivering the power at a frequency offset from the resonant frequency.

7. The ultrasonic dental scaler apparatus of claim 6 wherein the detection logic and memory include a programmable microprocessor with memory elements.

8. A method of using a computer controlled ultrasonic dental scaler comprising:

inserting a magnetostrictive dental scaler tip system in a hand piece, the system including a distal tip;

activating a controller to sweep a range of frequencies and determine a peak power transfer point of the tip system;

setting an offset from the peak power transfer point; and applying the distal tip to the surface of a tooth to be cleaned.

9. A method for using an ultrasonic dental scaler apparatus comprising conductors to an ultrasonic dental scaler, a power amplifier coupled to said conductors for delivery of variable power at variable frequency, a sweep oscillator coupled to said power amplifier for stepping the frequency from a preset low to a preset high to determine a primary resonant frequency of the ultrasonic dental scaler, and detection logic and memory to lock on to the resonant frequency detected and to store the value of the resonant frequency, comprising:

coupling the power amplifier to the conductors to the ultrasonic dental scaler;

coupling the sweep oscillator to the power amplifier;

detecting the resonant frequency;

storing the value of the resonant frequency;

setting an offside from the resonant frequency to reduce power transferred to the tip.

10. The method of claim 9, further comprising applying a distal tip of the apparatus to the surface of a tooth.

11. The method of claim 10, further comprising setting an offside from the resonant frequency to reduce power transferred to the tip.

12. A method for using a computer controlled ultrasonic dental scaler comprising:

inserting a magnetostrictive dental scaler system in a handpiece, wherein the system includes a distal tip;

activating the dental scaler controller to sweep a range of frequencies and determine a peak power transfer point;

setting an offset from the peak power transfer point; and applying the distal tip to the surface of a tooth.

\* \* \* \* \*

UNITED STATES PATENT AND TRADEMARK OFFICE
CERTIFICATE OF CORRECTION

PATENT NO. : 6,503,081 B1
DATED : January 7, 2003
INVENTOR(S) : James Feine

It is certified that error appears in the above-identified patent and that said Letters Patent is hereby corrected as shown below:

In the drawings, delete sheet 2, Figure 1 and replace with Figure 2 on the attached page.

Signed and Sealed this

Eighth Day of July, 2003

JAMES E. ROGAN
*Director of the United States Patent and Trademark Office*